United States Patent [19]
Okauchi et al.

[11] 3,941,879
[45] Mar. 2, 1976

[54] METHOD FOR INCREASING YIELD OF SILKWORM COCOONS EMPLOYING JUVENILE AND MOULTING HORMONES

[75] Inventors: Tetsuo Okauchi; Shoji Takamuku, both of Osaka; Saburo Tamura, Tokyo; Seifun Chou, Kobe, all of Japan

[73] Assignees: Takeda Chemical Industries, Ltd., Osaka; Nihon Tokushu Noyaku Seizo Kabushiki Kaisha, Tokyo, both of Japan

[22] Filed: Dec. 13, 1973

[21] Appl. No.: 424,316

[30] Foreign Application Priority Data
Dec. 28, 1972  Japan................................ 47-1656

[52] U.S. Cl. ............... 424/240; 424/278; 424/282; 424/312; 424/337; 424/340; 424/341

[51] Int. Cl.² ..................................... A61K 31/56
[58] Field of Search.................... 424/240, 282, 278

[56] References Cited
OTHER PUBLICATIONS

Chemical Abstracts, Vol. 76 (1972), p. 81444s.
Chemical Abstracts, Vol. 75 (1971), p. 95,935u.

*Primary Examiner*—V. D. Turner
*Attorney, Agent, or Firm*—Wenderoth, Lind & Ponack

[57] ABSTRACT

Quality silkworm cocoons are obtained in a high yield per unit rearing time and per unit amount of feedstuff by administering insect juvenile hormonal factors to the silkworm larvae at an early stage of their final instar and administering insect moulting hormonal factors at a later stage of their final instar.

3 Claims, No Drawings

METHOD FOR INCREASING YIELD OF SILKWORM COCOONS EMPLOYING JUVENILE AND MOULTING HORMONES

This invention relates to a method for increasing the yield of cocoons.

More particularly, the invention relates to an efficient method for producing quality silkworm cocoons which comprises dosing silkworm larvae with an insect juvenile hormonal factor (hereinafter referred to as "JH") in an early stage of their final instar and an insect moulting hormonal factor (hereinafter referred to as "MH") in a later stage of said instar.

Heretofore, for the purpose of enhancing the yield of silkworm cocoons, there have been made studies on artificial feeds, improvements in the breeding and selection of mulberry trees and in methods for the cultivation of mulberry trees, as well as improvements in the breeding and selection of improved races of silkworms and in methods for rearing them.

Recently, various attempts have been made to apply varieties of insect hormones and their related compounds to sericulture. For example, the present inventors have for some time studied the possibility of using MH as agents to render the time of moulting or maturation uniform. Further, attempts have been made to use JH as cocoon yield improvers.

However, the use of JH in practical applications often leads to unstable results, for the activities of JH are influenced in subtle ways by the growth stage of silkworms, among other conditions, and as a consequence, it is not only difficult to predict the growth pattern of silkworms but the variance of their growth is rather increased.

Furthermore, even if the yields of cocoons are enhanced by the use of JH, the accompanying delayed mounting causes reductions in cocoon production per rearing period and in feed efficiency and, accordingly, fully satisfactory results have not been realized as yet.

The intensive research undertaken by the present inventors to overcome these difficulties led to the finding that when JH is administered to silkworm larvae in an early stage of their final instar and MH is administered to them in a later stage of the same instar, the yield of cocoons per unit amount of feedstuff, namely, feed efficiency, is remarkably increased.

The term "JH" as used throughout the specification, means all hormonal substances preventing silkworm larvae from their metamorphosis JH includes, among others: 3,4-Methylenedioxyphenyl derivatives of formula (I)

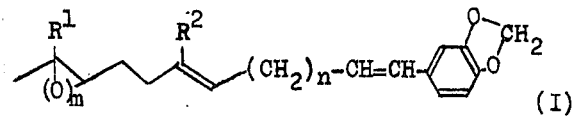

wherein $R^1$ and $R^2$, respectively, stands for a lower alkyl group of 1 to 4 carbon atoms; m is equal to zero or 1; and n is equal to zero, 1 or 2, such as:
1. 1-(3,4-Methylenedioxyphenyl)-5,9-dimethyl-8-epoxy-1,4-decadiene,
2. 1-(3,4-Methylenedioxyphenyl)-5,9-dimethyl-8-epoxy-1,4-undecadiene; Methyl 2,6-undecadienoate derivatives of general formula (II):

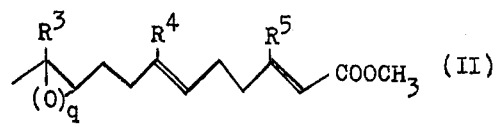

wherein $R^3$, $R^4$ and $R^5$, respectively, stand for a lower alkyl group of 1 to 4 carbon atoms; and q is equal to zero or 1, such as:
3. Methyl 3,7,11-trimethyl-10-epoxy-2,6-dodecadienoate,
4. Methyl 3,11-dimethyl-7-ethyl-10-epoxy-2,6-tridecadienoate,
5. Methyl 3,11-dimethyl-7-ethyl-10-epoxy-2,6-dodecadienoate;

and phenylethers or phenylthioethers of geraniol derivatives of general formula (III)

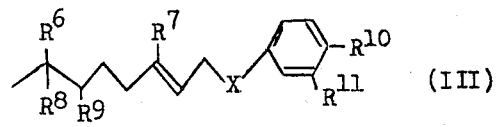

wherein $R^6$ and $R^7$, respectively, stand for a lower alkyl group of 1 to 4 carbon atoms; $R^8$ is chlorine atom or an alkoxy group of 1 to 4 carbon atoms, $R^9$ is hydrogen atom or $R^8$ and $R^9$, taken together, represent oxygen atom; X stands for oxygen or sulfur atom; $R^{10}$ stands for a lower alkyl group of 1 to 4 carbon atoms, nitro group, halogen atom or an alkoxycarbonyl group of 1 to 5 carbon atoms, $R^{11}$ stands for hydrogen atom or $R^{10}$ and $R^{11}$, taken together, represent methylenedioxy group, such as:
6. 2,6-dimethyl-2-epoxy-octa-6-ene-(3,4-methylenedioxyphenyl)-ether,
7. 2,6-Dimethyl-2-epoxy-octa-6-ene-(3,4-methylenedioxyphenyl)-thioether,
8. 3-Methyl-7-ethyl-3-epoxy-nona-7-ene-(3,4-methylenedioxyphenyl)-ether,
9. 3,7-Dimethyl-3-epoxy-nona-7-ene-(3,4-methylenedioxyphenyl)-ether,
10. 2,6-Dimethyl-2-epoxy-octa-6-ene-(4-ethyl-phenyl)-ether,
11. 2,6-Dimethyl-2-epoxy-octa-6-ene-(4-nitro-phenyl)-ether,
12. 2,6-Dimethyl-2-epoxy-octa-6-ene-(4-methylcarbo-nylphenyl)-ether,
13. 2,6-Dimethyl-2-epoxy-octa-6-ene-(4-chloro-phenyl)-ether,
14. 2,6-Dimethyl-2-ethoxy-octa-6-ene-(4-nitro-phenyl)-ether and so on.

These JHs are extracted and isolated from naturally occurring materials including insects, plants, microorganisms, etc. or can be chemically synthesized. [C.F. Chang and S. Tamura, Agr. Biol. Chem. 35, 1307 (1971), Dahm et al, Journal of the American Chemical Society, 89, 5292 (1967) and K. Mori et al, Tetrahedron 25, 1667 (1969)].

In case of applying JHs to silkworms, they are diluted with water or an organic solvent, with or without aid of a surfactant, to treat the body surface of silkworm, or the are added to mulberry leaf or artificial diet to feed silkworm. The organic solvent includes an alcohol such as methanol, ethanol, propanol, an ether such as ethyl ether, dioxane, a ketone such as acetone, isophorone, aliphatic hydrocarbon such as n-hexane. The treatment of the body surface may be conducted by spraying larvae with the dilution as mentioned above or by dipping larvae in the dilution. As the surfactants, there may be employed ones which are least harmless to silkworms, such as polyoxyethylene higher alcohol ethers, polyoxyethylene fatty acid esters and polyoxyethylene sorbitan fatty acid ester.

JH is administered to silkworms in an early stage during their final instar, preferably 24 to 96 hours after the start of feeding for the final instar and, for still better results, 48 to 72 hours after said start of feeding. Although the dosage depends upon the type of JH and the method or route of administration, it, in general, ranges from 0.01 to 100 μg. of JH per larva when it is administered orally and, for better results, 0.1 to 1.5 μg. on the same basis. In other words, the dosage is preferably such that it will extend the duration of the final instar at least by 24 hours over the period that would be prevailing should JH not be administered.

The term "MH" as used throughout the specification means all substances inducing silkworm larvae of the final instar to metamorphose into pupae, and the MH includes α-ecdysone, β-ecdysone, inokosterone, cyasterone, ponasterone A, ponasterone B, etc., and materials obtainable by processing plants containg MH. Among plants containing MH are the entire tissues or underground portions of plants of the family Amaranthaceae, such as *Achyranthes fauriei* LEV. et VAN, *Achyranthes longifolia* MAKINO, *Cyathula capitata* MOQUIN-TANDON, etc., the foliages of plants of the family Podocarpaceae, such as *Podocarpus Nakaii* HAY, *Podocarpus macrophyllus* D. DON, *Podocarpus chinensis* WALL., *Podocarpus Nagi* ZOLL. et MORTZ., etc.; the foliages of plants of the family Taxaceae, such as *Taxus cuspidata* SIEB. et ZUCC., *Taxus cuspidata var. nana* RHED., etc.; the aerial and underground portions of plants of the family Labiatae, such as *Ajuga decumbens* THUNB., *Ajuga incisa* MAXIM., *Ajuga nipponensis* MAKINO, etc.; and the underground portions of plants of the family Polypodiaceae, such as *Polypodium japonicum* MAKINO, *Polypodium nipponicum* METT., *Blechnum nipponicum* MAKINO, *Dryopteris thelypteris* BORY, etc. and various processed matters originating from these plants, which silkworms can bite and swallow without trouble. Included, thus, are the preparations which have been obtained by processing said MH or plant segments containing MH into forms which can be evenly incorporated in silkworm feed, for example, by drying and comminuting them directly into powders or extracting them with solvents such as water, alcohols (e.g. methanol, ethanol, aqueous butanol etc.).

While the dosage varies with types of MH, the preferred range is from 0.1 to 50 μg. per larva.

Though the time of dosing should be selected according to the stage of growth of silkworm larvae and the desired cocoon weight, the period from 110 to 288 hours after the start of feeding for the final instar under ordinary rearing conditions (23° to 27°C) is, in general, beneficial. Still better results are obtained when larvae are caused to ingest MH at or after the time when about 10 percent of them would reach the stage of maturity should JH not be administered, that is, in the period from 132 to 240 hours after the start of feeding for the final instar.

Compared with the known rearing methods, the present method brings about positive and significant increases in cocoon shell production per unit rearing time and per unit amount of feedstuff and also leads to improvements in quality of cocoons.

Throughout the specification and claims, the abbreviations "kg.", "g.", "cg.", "mg.", "μg.", "ppm", "%", "°C" and "hr." respectively refer to "kilogram(s)", "gram(s)", "centigram(s)", "milligram(s)", "microgram(s)", "part(s) per million", "percent", "degree centigrade" and "hour(s)".

EXAMPLE 1

Silkworm larvae (race: Kinshu x Showa) were reared using the following basal feed through their 1st to 4th instar.

| Basal feed | (weight part) |
|---|---|
| mulberry leaf powder | 20.0 |
| defatted soybean meal | 15.0 |
| cellulose powder | 35.5 |
| potato starch | 15.0 |
| β-sitosterol | 0.5 |
| Wesson's salt mixture* | 1.0 |
| vitamin B complex | a small part |
| sucrose | 10.0 |
| vitamin C | a small part |
| inositol | 0.5 |
| dipotassium hydrogen phosphate | 0.5 |
| choline chloride | 0.05 |
| dihydrostreptonycin | 0.1 |
| water | 200.0 |

*Wesson's salt mixture consists of the following minerals.

| | Weight part |
|---|---|
| NaCl | 105.0 |
| KCl | 120.0 |
| $KH_2PO_4$ | 310.0 |
| $Ca_3(PO_4)_2$ | 149.0 |
| $CaCO_3$ | 210.0 |
| $MgSO_4$ | 90.0 |
| $FePO_4.4 H_2O$ | 14.7 |
| $MnSO_4$ | 0.20 |
| $K_2Al_2(SO_4)_4.24 H_2O$ | 0.09 |
| $CuSO_4.5 H_2O$ | 0.39 |
| NaF | 0.57 |
| KI | 0.05 |

Immediately after their ecdysis for the last instar, the silkworms were divided into 16 groups of 100 larvae each. At the times indicated in Table I-(1), the larvae were put for 24 hours on rations prepared by adding 1-(3,4-methylenedioxyphenyl)-5, 9-dimethyl-8-epoxy-1,4-decadiene as JH to the basal feed in a concentration of 2 ppm on a dry weight basis. Then, at the times indicated in Table I-(1), the silkworm larvae were put on rations prepared by adding β-ecdysone as MH to the basal feed in a concentration of 10 ppm on a dry weight basis and reared with the feed till mounting.

The ingested amount per larva of 1-(3,4-methylenedioxyphenyl)-5,9-dimethyl-8-epoxy-1,4-decadiene was 1 to 1.5 μg, and the ingested amount per larva of β-ecdysone was 2 to 4 βg.

The rearing was performed at 25.5°C and 65% relative humidity.

The results are shown in Table I-(2) and (3).

The supplementation of feed with both JH and MH causes remarkable increase in cocoon shell production per unit rearing time. This tendency is particularly pronounced when these groups are compared with the groups to which JH alone was given.

Further, whereas the addition of JH after 72 hours following the start of feeding for the final instar tends to lower the percentage of reelable cocoons, no reduction is encountered in the percentage of reelable cocoons when MH is added to feed in an optional stage during the period from 160 to 220 hours after the start of feeding for the final instar.

When MH was added to the feed in combination with JH, there is noted a close correlation between the time of addition of MH and the cocoon shell weight, reelable cocoon weight and rearing time. Thus, by feeding MH to silkworm larvae in an optional stage after 160 hours following the start of feeding for the final instar, the rearing time can be freely controlled and, accordingly, it is even possible to obtain cocoons of optional size.

Table I — (1)

| Group No. | Period of feeding JH (hours after start of feeding for final instar) | Period of feeding MH (hours after start of feeding for final instar) |
|---|---|---|
| 1 | not added | not added |
| 2 | " | 160 and onward |
| 3 | 24 – 48 | not added |
| 4 | " | 160 and onward |
| 5 | " | 172 and onward |
| 6 | " | 184 and onward |
| 7 | 48 – 72 | not added |
| 8 | " | 160 and onward |
| 9 | " | 172 and onward |
| 10 | " | 184 and onward |
| 11 | " | 196 and onward |
| 12 | 72 – 96 | not added |
| 13 | " | 160 and onward |
| 14 | " | 172 and onward |
| 15 | " | 184 and onward |
| 16 | " | 196 and onward |
| 17 | " | 208 and onward |
| 18 | " | 220 and onward |

Table I — (2)

| Group No. | note(1) Rearing time for final instar (hr.) | Percentage of reelable cocoons (%) | note(2) Reelable cocoon weight (g.) | note(3) Cocoon shell weight (mg.) |
|---|---|---|---|---|
| 1 | 178 | 100 | 1.70 | 412 |
| 2 | 170 | 100 | 1.69 | 403 |
| 3 | 205 | 98 | 1.92 | 465 |
| 4 | 178 | 98 | 1.82 | 438 |
| 5 | 189 | 97 | 1.96 | 470 |
| 6 | 191 | 97 | 1.95 | 472 |
| 7 | 220 | 100 | 2.05 | 498 |
| 8 | 178 | 99 | 1.80 | 436 |
| 9 | 189 | 100 | 1.92 | 468 |
| 10 | 195 | 98 | 2.07 | 500 |
| 11 | 204 | 98 | 2.08 | 505 |
| 12 | 254 | 93 | 2.38 | 569 |
| 13 | 181 | 98 | 1.81 | 441 |
| 14 | 191 | 97 | 1.95 | 471 |
| 15 | 204 | 99 | 2.11 | 503 |
| 16 | 211 | 95 | 2.20 | 531 |
| 17 | 224 | 95 | 2.33 | 560 |
| 18 | 232 | 94 | 2.36 | 572 |

Table I — (3)

| Group No. | note(3) Cocoon shell weight per unit rearing time (mg./hr.) | Index | | |
|---|---|---|---|---|
| | | note(4) | | |
| 1 | 2.3146 | 100 | | |
| 2 | 2.3706 | 102 | | |
| | | | note(5) | |
| 3 | 2.2683 | 98 | 100 | |
| 4 | 2.4607 | 106 | 108 | |
| 5 | 2.4868 | 107 | 110 | |
| 6 | 2.4712 | 107 | 109 | |
| | | | note(6) | |
| 7 | 2.2636 | 98 | 100 | |
| 8 | 2.4494 | 106 | 108 | |
| 9 | 2.4762 | 107 | 109 | |
| 10 | 2.5641 | 111 | 113 | |
| 11 | 2.4755 | 107 | 109 | |
| | | | | note(7) |
| 12 | 2.2400 | 97 | | 100 |
| 13 | 2.4365 | 105 | | 109 |
| 14 | 2.4660 | 107 | | 110 |
| 15 | 2.4657 | 107 | | 110 |
| 16 | 2.5166 | 109 | | 112 |
| 17 | 2.5000 | 108 | | 112 |
| 18 | 2.4655 | 107 | | 110 | note(1): The period from the start of feeding for the final instar to the time when the emergence of matured silkworm larvae reached 50 percent was taken as the rearing time for the final instar.

note(2): The reelable cocoon weight and cocoon shell weight are averages for equal numbers of male and female silkworms.

note(3): Cocoon shell weight per unit rearing time (mg./hr.) $= \dfrac{\text{cocoon shell weight (mg.)}}{\text{final instar rearing time (hr.)}}$ note(4): The index of cocoon shell weight per unit rearing time with the corresponding figure for control (Group 1) being taken as 100.

note(5) to (7): The indexes of cocoon shell weight per unit rearing time with the weights for Groups 3, 7 and 12, to which JH was added, being taken respectively as 100.

EXAMPLE 2

Silkworm larvae (race: Kinshu x Showa) were reared using a basal feed of the same composition as that described in Example 1 and, 48 hours after the start of feeding for 5th instar, divided into 11 groups of 100 larvae each. The silkworms were put for 24 hours on rations prepared by adding four different types of JH to basal feed in the predetermined concentrations shown in Table II. Thereafter, the larvae were further placed on the basal feed for 132 hours. Then, 204 hours after the start of feeding for 5th instar and onward, the larvae were put on rations prepared by adding three different MHs in varying concentrations to the basal feed and reared till mounting.

Other rearing conditions and the items studied are the same as those set forth in Example I.

The results obtained are shown in Table II.

Irrespective of the type of JH and the type of MH, the combined administration of JH and MH invariably resulted in improvements in cocoon shell production per unit rearing time. This tendency is particularly pronounced when these results for these groups are compared with the results for the groups to which JH alone was added.

Table II

| Group No. | Type and concentration in feed of JH | | Type and concentration in feed MH | | Rearing time of final instar (hr.) | Percentage of reelable cocoons (%) | Reelable cocoon weight (g.) | Cocoon shell weight (mg.) | Cocoon shell weight per unit rearing time (mg./hr.) | Index |
|---|---|---|---|---|---|---|---|---|---|---|
| 1 | not added | | not added | | 182 | 96 | 1.70 | 381 | 2.0934 | 100 |
| 2 | (1)* | 3 ppm | not added | | 246 | 95 | 2.29 | 514 | 2.0894 | 100 |
| 3 | (1)* | 3 ppm | β-ecdysone | 10 ppm | 220 | 97 | 2.26 | 505 | 2.2954 | 110 |
| 4 | (1)* | 3 ppm | Ponasterone A | 8 ppm | 222 | 96 | 2.26 | 507 | 2.2841 | 109 |

Table II-continued

| Group No. | Type and concentration in feed of JH | | Type and concentration in feed MH | Rearing time of final instar (hr.) | Percentage of reelable cocoons (%) | Reelable cocoon weight (g.) | Cocoon shell weight (mg.) | Cocoon shell weight per unit rearing time (mg./hr.) | Index |
|---|---|---|---|---|---|---|---|---|---|
| 5 | (1)* | 3 ppm | Inokosterone 40 ppm | 219 | 95 | 2.24 | 500 | 2.2831 | 109 |
| 6 | (2)* | 2 ppm | not added | 263 | 94 | 2.39 | 531 | 2.0190 | 96 |
| 7 | (2)* | 2 ppm | β-ecdysone 10 ppm | 220 | 96 | 2.29 | 510 | 2.3181 | 111 |
| 8 | (10)* | 1.5 ppm | not added | 246 | 93 | 2.30 | 512 | 2.0813 | 99 |
| 9 | (10)* | 1.5 ppm | β-ecdysone 10 ppm | 223 | 96 | 2.24 | 503 | 2.2556 | 108 |
| 10 | (4)* | 100 ppm | not added | 252 | 92 | 2.29 | 510 | 2.0238 | 97 |
| 11 | (4)* | 100 ppm | β-ecdysone 10 ppm | 222 | 95 | 2.24 | 499 | 2.2477 | 107 |

*The numbers assigned to various JHs correspond to the compound numbers given hereinbefore.

EXAMPLE 3

Silkworm larvae (race: Gunka x Hoshun) were reared using the basal feed as described in Example 1 through the 1st to 4th instars and, 48 hours after the start of feeding for the 5th instar, divided into 8 groups of 100 larvae each. As shown in Table III, the silkworm in groups 2 through 8 were then put for 24 hours on rations prepared by adding 1-(3,4-methylenedioxyphenyl)-5,9-dimethyl-8-epoxy-1,4-decadiene as JH to the basal feed in a concentration of 4 ppm on a dry weight basis. Then, the silkworms were put again on the basal feed. Thereafter, 184 hours after the start of feeding for the 5th instar and onward till mounting, the larvae were reared using rations prepared by adding β-ecdysone to the basal feed in the various concentrations indicated in Table III.

Other rearing conditions and items studied were the same as those in Example 1.

The results obtained are set forth in Table III.

The combined administration of JH and MH brought about remarkably significant gains in cocoon shell production per unit rearing time. Further, while this tendency was pronounced when the concentration of β-ecdysone was 5 ppm or higher, the percentage of reelable cocoons suffered slight drops when the concentrations of β-ecdysone was as high as 40 ppm or more.

through 1st to 4th instars and, 48 hours after the start of feeding for the 5th instar, were divided into 13 groups of 50 larvae each.

As shown in Table IV-(1), the larvae were put for 24 hours on rations prepared by adding 1-(3,4-methylenedioxyphenyl)-5,9-dimethyl-8-epoxy-1,4-decadiene as JH to the basal feed in various concentrations. Thereafter, the larvae were put again on the basal feed alone, after which time they were put, at the times indicated in Table IV-(1), on rations prepared by adding β-ecdysone as MH to the basal feed in a concentration of 10 ppm on a dry weight basis and reared till mounting.

The rearing periods in the 5th instar were measured and the amounts of feed intake on a dry weight basis during these periods were calculated from the amounts of feed residues.

The results obtained are shown in Table IV-(1) and (2).

The group to which MH had been added showed a slight decrease in cocoon shell weight and while the groups dosed with JH alone yielded increased cocoon shell weight, they showed apparent decrease in cocoon shell production per unit rearing time and in feed efficiency.

In contrast, the combined administration of JH and MH resulted in significant increase in cocoon shell Table III

| Group No. | JH (ppm) | MH (ppm) | Rearing time of 5-instar (hr.) | Percentage of reelable cocoons (%) | Reelable cocoon weight (g.) | Cocoon shell weight (mg.) | Cocoon shell weight per unit rearing time(mg./hr.) | Index | |
|---|---|---|---|---|---|---|---|---|---|
| 1 | 0 | 0 | 188 | 99 | 1.76 | 418 | 222 | 100 | — |
| 2 | 4 | 0 | 228 | 100 | 2.11 | 501 | 220 | 99 | 100 |
| 3 | 4 | 2.5 | 220 | 100 | 2.09 | 500 | 227 | 102 | 103 |
| 4 | 4 | 5 | 211 | 100 | 2.10 | 498 | 236 | 106 | 107 |
| 5 | 4 | 10 | 204 | 99 | 2.06 | 489 | 240 | 108 | 109 |
| 6 | 4 | 20 | 204 | 100 | 2.07 | 486 | 238 | 107 | 108 |
| 7 | 4 | 40 | 201 | 96 | 2.07 | 481 | 239 | 108 | 109 |
| 8 | 4 | 80 | 200 | 87 | 2.09 | 472 | 236 | 106 | 107 |

EXAMPLE 4

Silkworm larvae (race: Gunka x Hoshun) were reared using the basal feed described in Example 1 production per unit rearing time and feed efficiency.

Table IV — (1)

| Group No. | Concentration of JH (ppm) | Time of adding MH (hours after start of feeding for 5-instar) | Average rearing period of 5-instar (hr.) | Feed intake during 5-instar for 100 silkworms (g.) |
|---|---|---|---|---|
| 1 | 0 | not added | 184 | 356 |
| 2 | 0 | 169 and onward | 178 | 341 |
| 3 | 1 | not added | 206 | 417 |
| 4 | 1 | 193 and onward | 194 | 380 |
| 5 | 2 | not added | 228 | 459 |
| 6 | 2 | 193 and onward | 202 | 388 |

Table IV — (1)-continued

| Group No. | Concentration of JH (ppm) | Time of adding MH (hours after start of feeding for 5-instar) | Average rearing period of 5-instar (hr.) | Feed intake during 5-instar for 100 silkworms (g.) |
|---|---|---|---|---|
| 7 | 4 | not added | 246 | 501 |
| 8 | 4 | 193 and onward | 203 | 385 |
| 9 | 4 | 217 and onward | 219 | 425 |
| 10 | 8 | not added | 262 | 578 |
| 11 | 8 | 193 and onward | 204 | 403 |
| 12 | 8 | 217 and onward | 224 | 445 |
| 13 | 8 | 241 and onward | 249 | 527 |

Table IV — (2)

| Group No. | Percentage of reelable cocoons (%) | Cocoon weight, average for male and female (g.) | Cocoon shell weight, average for male and female (g.) | note(1) Cocoon shell production per unit rearing time (mg./hr.) | Index | note(2) Feed efficiency | Index |
|---|---|---|---|---|---|---|---|
| 1 | 99 | 1.82 | 400 | 2.1739 | 100 | 1.1235 | 100 |
| 2 | 98 | 1.77 | 388 | 2.1797 | 100 | 1.1378 | 101 |
| 3 | 99 | 2.01 | 451 | 2.1893 | 101 | 1.0815 | 96 |
| 4 | 99 | 1.99 | 443 | 2.2835 | 105 | 1.1657 | 104 |
| 5 | 98 | 2.20 | 497 | 2.1798 | 100 | 1.0827 | 96 |
| 6 | 99 | 2.19 | 490 | 2.4257 | 112 | 1.2628 | 112 |
| 7 | 97 | 2.37 | 518 | 2.1056 | 97 | 1.0339 | 92 |
| 8 | 99 | 2.29 | 496 | 2.4433 | 112 | 1.2883 | 115 |
| 9 | 100 | 2.35 | 512 | 2.3378 | 107 | 1.2047 | 107 |
| 10 | 96 | 2.43 | 537 | 2.0496 | 94 | 0.9290 | 83 |
| 11 | 97 | 2.41 | 492 | 2.4117 | 111 | 1.2208 | 109 |
| 12 | 98 | 2.42 | 511 | 2.2812 | 105 | 1.1483 | 102 |
| 13 | 96 | 2.40 | 534 | 2.1445 | 99 | 1.0132 | 90 | note(1):

$$\text{Cocoon shell production per rearing time (mg/hr)} = \frac{\text{Cocoon shell weight, average for male and female silkworms (mg.)}}{\text{Average 5-instar rearing time (hr.)}}$$

note(2):

$$\text{Feed efficiency} = \frac{\text{Cocoon shell weight, average for male and female silkworms (mg.)}}{\text{Feed intake during 5-instar for 100 silkworms (g.)}}$$

EXAMPLE 5

Silkworm larvae (race: Shungetsu x Hosho) reared with fresh mulberry leaf in the routine manner were divided into 5 groups, 3,000 larvae per group; immediately after their ecdysis for 5th instar and put on mulberry leaves-on-shoots rations. Forty eight hours after the start of 5th instar feeding, suspension obtained by adding 1-(3,4-methylene-dioxy-phenyl)-5,9-dimethyl-8-epoxy-1,4-decadiene to a 1 % aqueous solution of polyoxyethylenesorbitan mono-oleate (Tween 20) to give a concentration of 250 ppm as indicated in Table V was sprayed over the larvae at the dose of 500 ml. per 3000 larvae. At the times indicated in Table V-(1), a 20 ppm aqueous solution of β-ecdysone was sprayed over at the dose of 500 ml. per 3,000 larvae.

The larvae were reared until the emergence of mature larvae had reached 50 %.

The average temperature prevailing during the 5th instar rearing period was 23.5°C.

The results are set forth in Table V-(1) and (2). Even when silkworms on a mulberry leaves-on-shoots ration were sprayed, the combined administration of JH and MH caused remarkable increases in cocoon shell production per unit rearing time and this tendency is more evident when the results are compared with the corresponding results obtained by employing JH alone. Similarly improved results were obtained in terms of total reelable cocoon yield per unit rearing time.

Table V — (1)

| Group No. | Time of adding JH (after start of feeding for 5-instar) | Time of adding MH (after start of feeding for 5-instar) | Number of reelable cocoons | Total reelable cocoon weight (kg.) | Rearing time (hr.) |
|---|---|---|---|---|---|
| 1 | not sprayed | not sprayed | 2,889 | 5.74 | 186 |
| 2 | not sprayed | sprayed, after 172 hr. | 2,903 | 5.95 | 186 |
| 3 | sprayed, after 48 hr. | not sprayed | 2,872 | 7.33 | 267 |
| 4 | sprayed, after 48 hr. | sprayed, after 184 hr. | 2,946 | 6.81 | 202 |
| 5 | sprayed, after 48 hr. | sprayed, after 196 hr. | 2,926 | 7.28 | 212 |

Table V — (2)

| Group No. | note (1) Cocoon weight (g.) | note (2) Cocoon shell weight (cg.) | Cocoon shell weight per unit rearing time (cg.) | Cocoon shell weight per unit rearing time (Index) | Total reelable cocoon weight per unit rearing time (g./hr.) |
|---|---|---|---|---|---|
| 1 | 1.92 | 47.0 | 0.2527 | 100 | 30.9 |
| 2 | 1.93 | 46.8 | 0.2530 | 100 | 32.0 |
| 3 | 2.33 | 58.9 | 0.2206 | 87 (100)* | 27.5 |
| 4 | 2.26 | 55.6 | 0.2753 | 109 (125)* | 33.7 |
| 5 | 2.33 | 58.2 | 0.2700 | 108 (123)* | 34.0 | note (1): Cocoon weight (g.) = $\left( \dfrac{\text{Total cocoon weight of 100 female silkworms}}{100} + \dfrac{\text{Total cocoon weight of 100 male silkworms}}{100} \right) \times \frac{1}{2}$ note (2): Cocoon shell weight (cg.) = $\left( \dfrac{\text{Total cocoon shell weight of 100 female silkworms}}{100} + \dfrac{\text{Total cocoon shell weight of 100 male silkworms}}{100} \right) \times \frac{1}{2}$

*Parenthetized are indexes with the result obtained by the use of JH alone being taken as 100.

What is claimed is:

1. A method for increasing the yield of silkworm cocoons which comprises administering to silkworm larvae, orally or through the body surface by means of spraying or dipping, an insect juvenile hormonal factor, which prevents silkworm larvae from metamorphosis, in an amount of from 0.01 to 100 μg.per silkworm larva in a period of from 24 to 96 hours after the start of feeding for their final instar, and administering to the silkworm larvae, orally or through the body surface by means of spraying or dipping, an insect moulting hormonal factor, which induces final-instar silkworm larvae to metamorphose into pupae, in an amount of from 0.1 to 50 μg.per silkworm larva in a period of from 110 to 288 hours after the start of feeding for the same instar, wherein the insect juvenile hormonal factor is selected from the group consisting of a compound of the formula

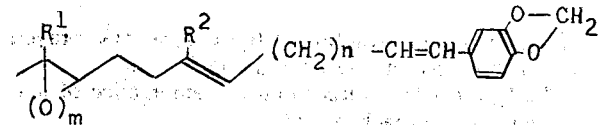

wherein $R^1$ and $R^2$, respectively, represent alkyl of 1 to 4 carbon atoms, m is zero or 1 and n is zero, 1 or 2; a compound of the formula

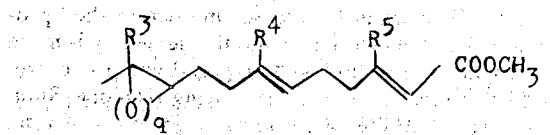

wherein $R^3$, $R^4$ and $R^5$ respectively, represent alkyl of 1 to 4 carbon atoms and q is zero or 1; and a compound of the formula

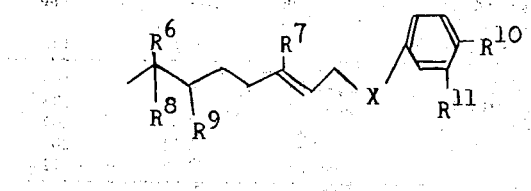

wherein $R^6$ and $R^7$, respectively, represent alkyl of 1 to 4 carbon atoms, $R^8$ represents chlorine or alkoxy of 1 to 4 carbon atoms, $R^9$ represents hydrogen, or $R^8$ and $R^9$, taken together, represent oxygen, X represents oxygen or sulfur, $R^{10}$ represents alkyl of 1 to 4 carbon atoms, nitro, halogen or alkoxycarbonyl of 1 to 5 carbon atoms, $R^{11}$ represents hydrogen, or $R^{10}$ and $R^{11}$, taken together, represent methylenedioxy, and the insect moulting hormonal factor is selected from the group consisting of α-ecdysone, β-ecdysone, inokosterone, cyasterone, ponasterone A and ponasterone B.

2. A method as claimed in claim 1, wherein the period of administering the insect hormonal factor is from 48 to 72 hours after the start of feeding for the final instar and the period of administering the insect moulting hormonal factor is from 132 to 240 hours after the start of feeding for the same instar.

3. A method as claimed in claim 1, wherein the insect juvenile hormonal factor is selected from the group consisting of 1-(3,4-methylenedioxyphenyl)-5,9-dimethyl-8- epoxy-1,4-decadiene, 1-(3,4-methylenedioxyphenyl)-5,9-dimethyl-8-epoxy-1,4-undecadiene, methyl 3,7,11-trimethyl-10-epoxy-2,6-dodecadienoate, methyl 3,11-dimethyl-7-ethyl-10-epoxy-2,6-tridecadienoate, methyl 3,11-dimethyl-7-ethyl-10-epoxy-2,6-dodecadienoate, 2,6-dimethyl-2-epoxy-octa-6-ene-(3,4-methyl-enedioxyphenyl)-ether, 2,6-dimethyl-2-epoxy-octa-6-ene- 3,4-methylenedioxyphenyl)-thioether, 3-methyl-7-ethyl-3-epoxynona-7-ene-(3,4,-methylenedioxyphenyl)-ether, 3,7-dimethyl-3-epoxy-nona-7-ene- 3,4-methylenedioxyphenyl)-ether, 2,6-dimethyl-2- epoxy-octa-6-ene-(4-ethyl-phenyl)-ether, 2,6-dimethyl -2-epoxy-octa-6-ene-(4-nitrophenyl)-ether, 2,6-dimethyl-2-epoxy-octa-6-ene-(4-methylcarbonylphenyl)-ether, 2,6-dimethyl -2-epoxy-octa-6-ene-(4-chlorophenyl)-ether and 2,6-dimethyl -2-ethoxy-octa-6-ene-(4-nitrophenyl)-ether.

* * * * *